United States Patent
Harvey et al.

(10) Patent No.: US 10,702,256 B2
(45) Date of Patent: *Jul. 7, 2020

(54) RETRACTOR SYSTEM HAVING AN ARTICULATED FRAME

(71) Applicant: Thompson Surgical Instruments, Inc., Traverse City, MI (US)

(72) Inventors: William Harvey, Traverse City, MI (US); Dan Farley, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 182 days.

This patent is subject to a terminal disclaimer.

(21) Appl. No.: 16/038,303

(22) Filed: Jul. 18, 2018

(65) Prior Publication Data

US 2018/0317897 A1 Nov. 8, 2018

Related U.S. Application Data

(63) Continuation of application No. 15/166,864, filed on May 27, 2016, now Pat. No. 10,028,735.

(60) Provisional application No. 62/167,619, filed on May 28, 2015.

(51) Int. Cl.
*A61B 17/02* (2006.01)
*A61B 90/50* (2016.01)

(52) U.S. Cl.
CPC .......... *A61B 17/02* (2013.01); *A61B 17/0206* (2013.01); *A61B 17/0293* (2013.01); *A61B 90/50* (2016.02)

(58) Field of Classification Search
CPC ...... A61B 17/02; A61B 90/50; A61B 17/0206
See application file for complete search history.

(56) References Cited

U.S. PATENT DOCUMENTS

| | | | |
|---|---|---|---|
| 4,949,707 A | 8/1990 | LeVahn et al. | |
| 4,971,037 A * | 11/1990 | Pelta .................. | A61B 17/0206 403/390 |
| 4,971,038 A | 11/1990 | Farley | |
| 4,989,587 A | 2/1991 | Farley | |
| 5,025,780 A | 6/1991 | Farley | |
| 5,365,921 A | 11/1994 | Bookwalter et al. | |
| 5,611,423 A * | 3/1997 | Graham ................. | B65G 27/08 198/757 |
| 5,888,197 A | 3/1999 | Mulac et al. | |
| 5,897,087 A | 4/1999 | Farley | |
| 5,902,233 A | 5/1999 | Farley et al. | |
| 5,984,865 A | 11/1999 | Farley et al. | |
| 6,017,008 A | 1/2000 | Farley | |
| 6,190,312 B1 * | 2/2001 | Fowler, Jr. ......... | A61B 17/0293 600/231 |

(Continued)

OTHER PUBLICATIONS

International Search Report and Written Opinion for PCT/US2016/34654, dated Aug. 25, 2016. (8 pages).

*Primary Examiner* — Christian A Sevilla
(74) *Attorney, Agent, or Firm* — McAndrews, Held & Malloy, Ltd.

(57) ABSTRACT

A surgical retractor system secured to a surgical operating table. The retractor system includes a single cross bar and a one-piece frame for positioning of surgical retractor blades relative to a surgical site.

18 Claims, 8 Drawing Sheets

(56) References Cited

U.S. PATENT DOCUMENTS

| | | | |
|---|---|---|---|
| 6,296,609 B1 * | 10/2001 | Brau | A61B 17/02 600/210 |
| 6,416,465 B2 | 7/2002 | Brau | |
| 6,511,423 B2 | 1/2003 | Farley | |
| 7,288,065 B1 | 10/2007 | Taylor et al. | |
| 7,309,312 B2 | 12/2007 | Bjork et al. | |
| 8,100,827 B2 | 1/2012 | Farley | |
| 8,257,255 B2 | 9/2012 | Farley et al. | |
| 8,360,971 B2 | 1/2013 | Farley et al. | |
| 8,617,064 B2 | 12/2013 | Farley | |
| 8,753,272 B2 | 6/2014 | Farley | |
| 2002/0077532 A1 * | 6/2002 | Gannoe | A61B 17/02 600/232 |
| 2011/0257487 A1 | 10/2011 | Thalgott et al. | |
| 2013/0204091 A1 | 8/2013 | Menendez et al. | |
| 2015/0018623 A1 | 1/2015 | Friedrich et al. | |
| 2015/0182211 A1 | 7/2015 | Nowak et al. | |

* cited by examiner

RETRACTOR SYSTEM HAVING AN ARTICULATED FRAME

BACKGROUND OF THE INVENTION

A retractor system's frame typically includes a rail clamp, a cross bar and two universal joints which are permanently mounted to the cross bar. In addition, two lateral arms, an extension arm and two universal joints may be added. Many surgical cases require only the use of two lateral arms. However, when the surgeon wishes to enclose the frame he secures the extension arm to the lateral arms with two universal joints. The enclosing of the frame thus requires five additional components to be added to the cross bar which is very versatile but time consuming to erect.

It is therefore an object of the present invention to provide the versatility while reducing the five components to one.

BRIEF SUMMARY OF THE INVENTION

A one piece frame includes lateral arms that connect a conventional extension arm of a surgical retractor frame. The one-piece frame allows the lateral arms to rotate 360 degrees making it possible for the surgeon to position the distal ends of the lateral arms in the cross bar. This gives versatility in positioning the frame's height relative to the patient without having to adjust the cross bar's height.

DETAILED DESCRIPTION OF AN EMBODIMENT

Figure 1:
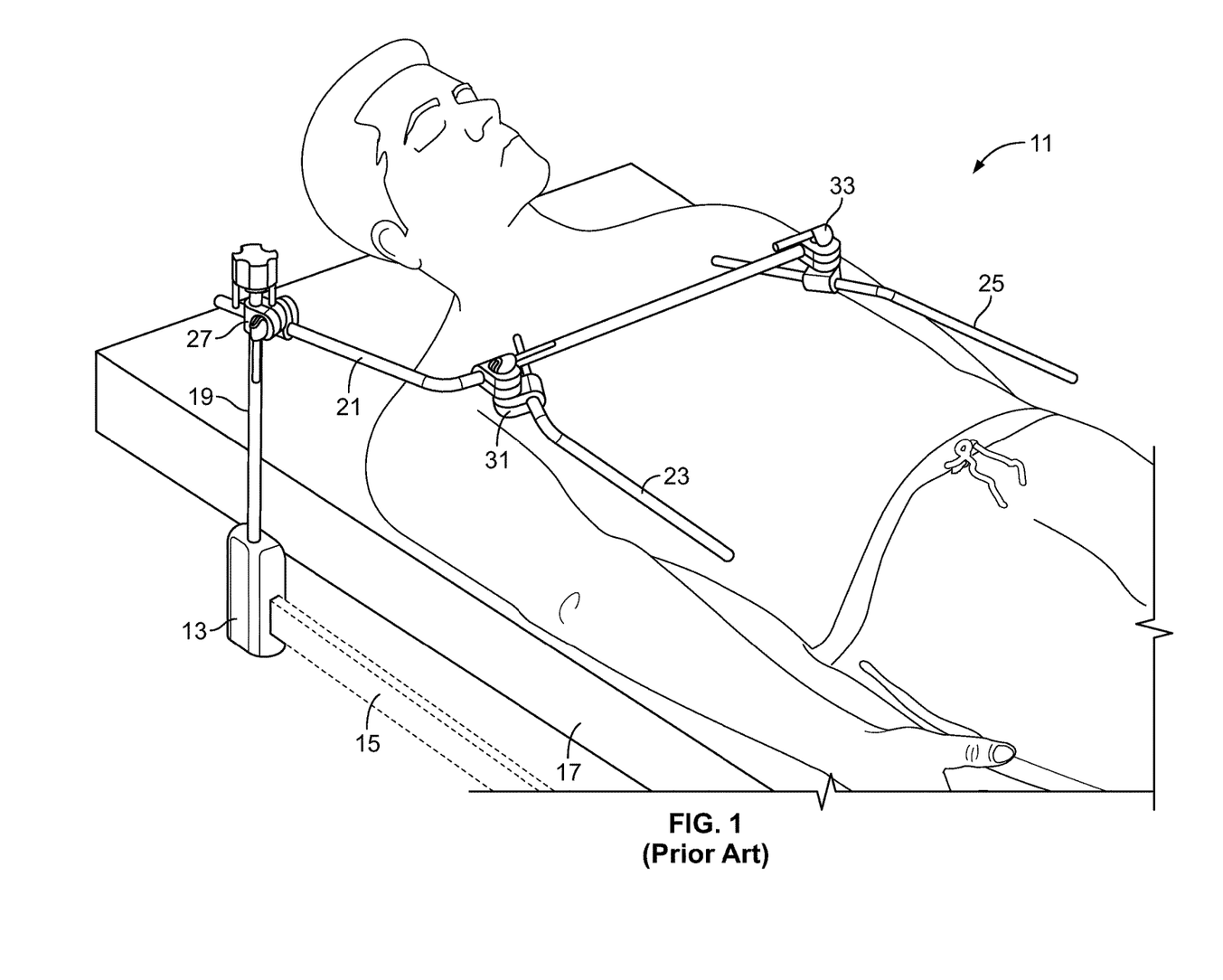
FIG. 1 is a perspective view of a retractor frame of the prior art.

Referring to FIG. 1, a conventional surgical retraction system 11 includes an adjustable rail clamp 13 which is securable to a horizontal rail 15 of a conventional operating table 17. A post 19 extends vertically from adjustable rail clamp 13 to provide support for a cross bar 21 which in turn provides support for a pair of lateral arms 23, 25. Cross bar 21 is secured to the post 19 by a universal joint clamp 27.

Lateral arms 23, 25 are respectively secured to the cross bar 21 by a pair of universal joint clamps 31, 33. Clamps 31, 33 are permanently mounted to cross bar 21.

Figure 2:
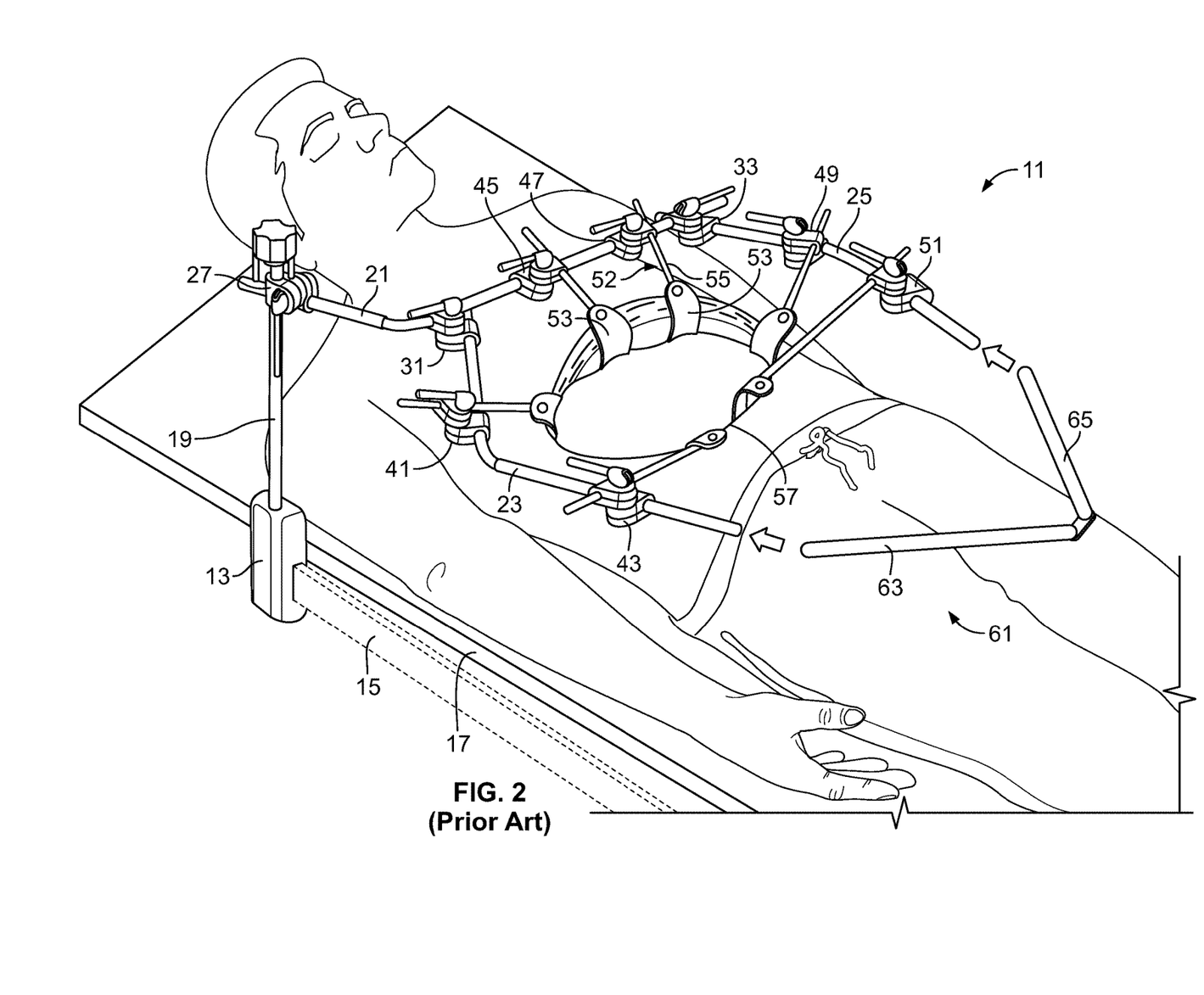
FIG. 2 is a perspective view of a retractor frame of FIG. 1 and additionally includes an extension arm.

As shown in FIG. 2, additional joint clamps 41, 43, 45, 47, 49, and 51 may be disposed along the cross bar 21 and along lateral arms 23, 25 for rigidly securing any number of retractor blades 52 to the cross bar and lateral arms.

Each retractor blade 52 may include a blade portion 53 and a retractor arm 55. The blade portion 53 preferably extends downwardly into an incision 57 made by a surgeon. The blade portion 53 may be used to retract anatomy so as to make the incision 57 accessible to the surgeon.

Figure 1A:
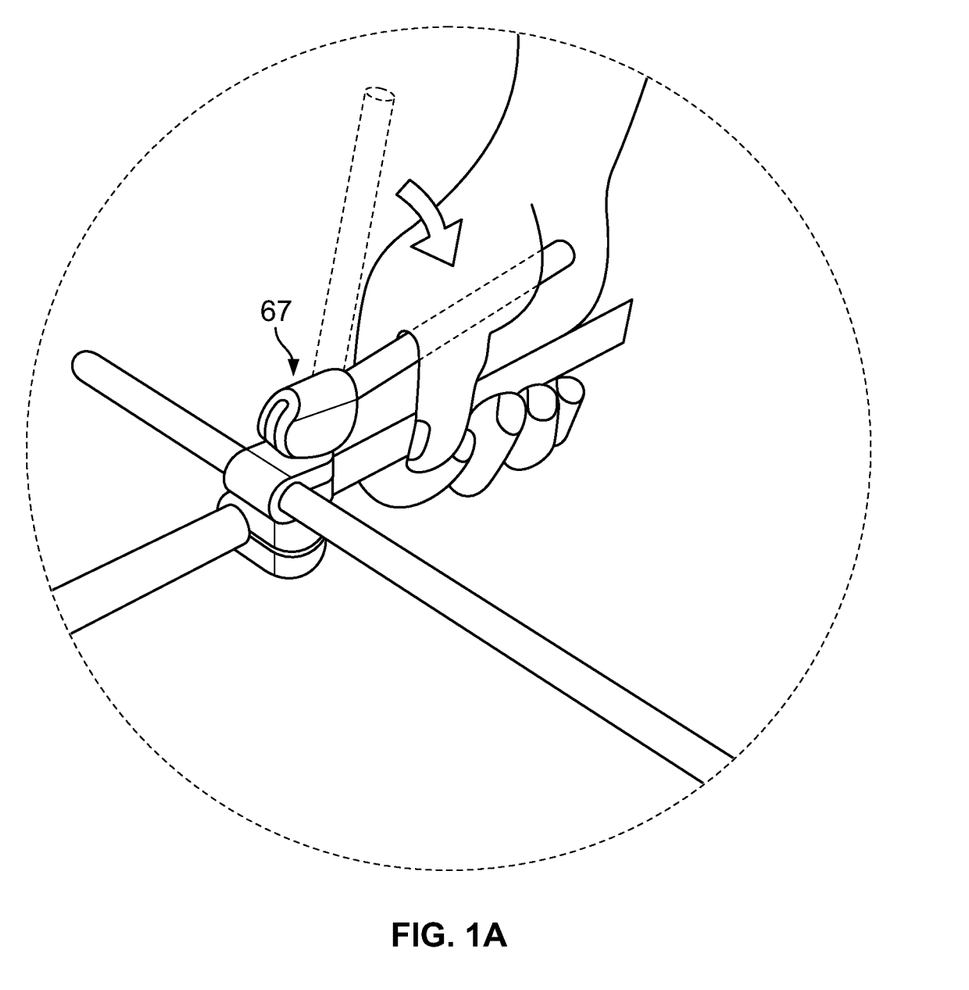
FIG. 1A is a perspective view of a convention universal joint.

As shown in FIG. 2, a generally V-shaped extension arm 61 may be used by a surgeon when the surgeon wishes to enclose the frame (i.e., the frame around the incision formed by cross bar 21 and lateral arms 23, 25). Extension arm 61 includes two straight arms 63, 65. Arms 63, 65 are to be secured to lateral arms 23, 25 using two separate universal joints 67, one being shown in FIG. 1A.

Figure 3:
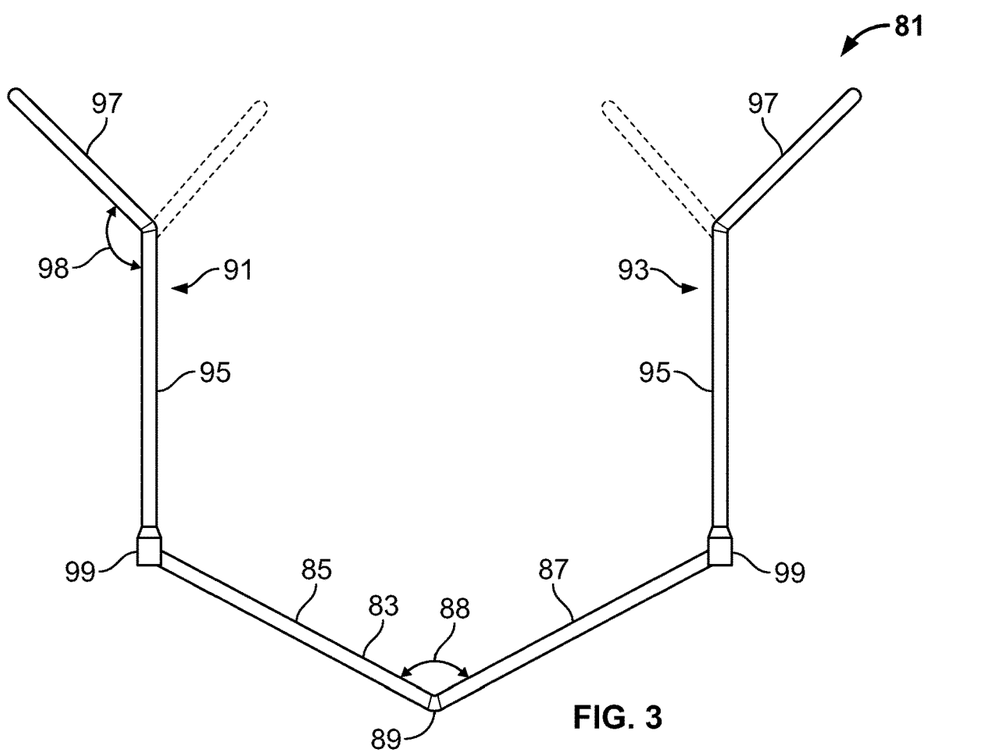
FIG. 3 is a top view of a one-piece frame for use with a conventional cross bar of FIG. 1.

Referring now to FIG. 3, a one-piece or articulated, integral frame 81 replaces lateral arms 23, 25 and extension arm 61, as well as two universal joints 67. In particular, the articulated frame 81 includes an extension bar 83 comprising two extension arms 85, 87. Each extension arm 85, 87 is cylindrical in shape, substantially straight and rigidly attached to one another at a bend 89. An obtuse angle 88 is formed between the two extension arms 85, 87.

The articulated frame 81 also includes a pair of lateral arms 91, 93. Each lateral arm 91, 93 is formed of two straight arm portions 95, 97 and an end portion 99. Arm portions 95, 97 are each cylindrical in shape and rigidly secured together at an obtuse angle 98.

Arm portion 97 may be formed integral with its respective straight arm portion 95. Each straight arm portion 95 terminates in an end portion 99 which is connected to a respective extension arm 85, 87. Arm portion 95 may rotate about its axis to move arm portion 97, for example, to the dotted line position 96, as described in detail below.

Figure 4:
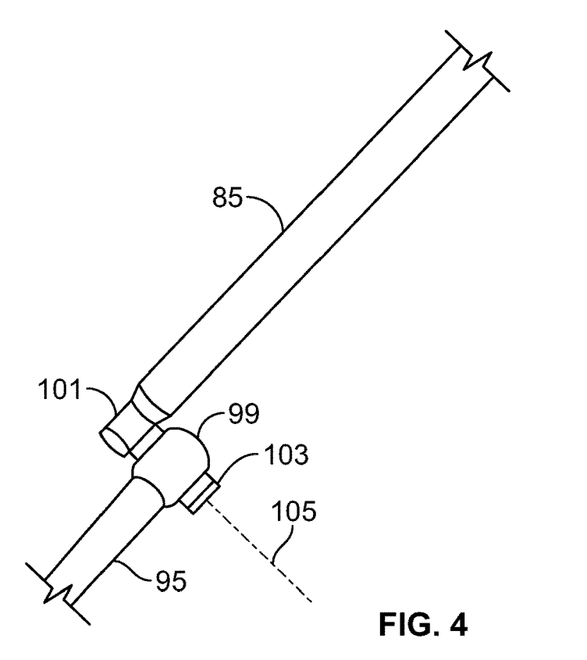
FIG. 4 is a side perspective view of an arm connection area of the one-piece frame of FIG. 3.

Referring now to FIG. 4, the end portion 99 of arm portion 95 is connected to an end 101 of extension arm 85. A pin 103 is secured to end 101 and extends laterally outwardly from end 101 to define an axis 105 about which arm portion 95 may fully rotate through 360 degrees. End 101 is shaped so as to allow free rotation of end portion 99 about axis 105.

Figure 5:
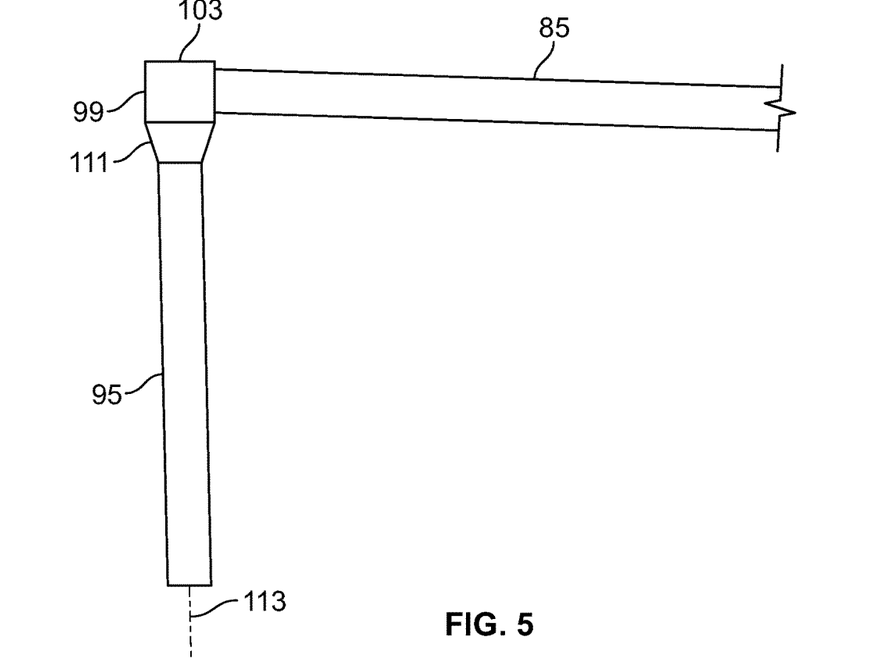
FIG. 5 is a top perspective view of the arm connection area of the one-piece frame of FIG. 3.

Referring to FIG. 5, end portion 99 is connected to a middle section 111 which in turn is connected to arm portion 95. The middle section 111 provides structure for connection of the arm portion 95 to pin 103 so as to provide rotation of arm portion 95 about its longitudinal axis 113.

Figure 6:
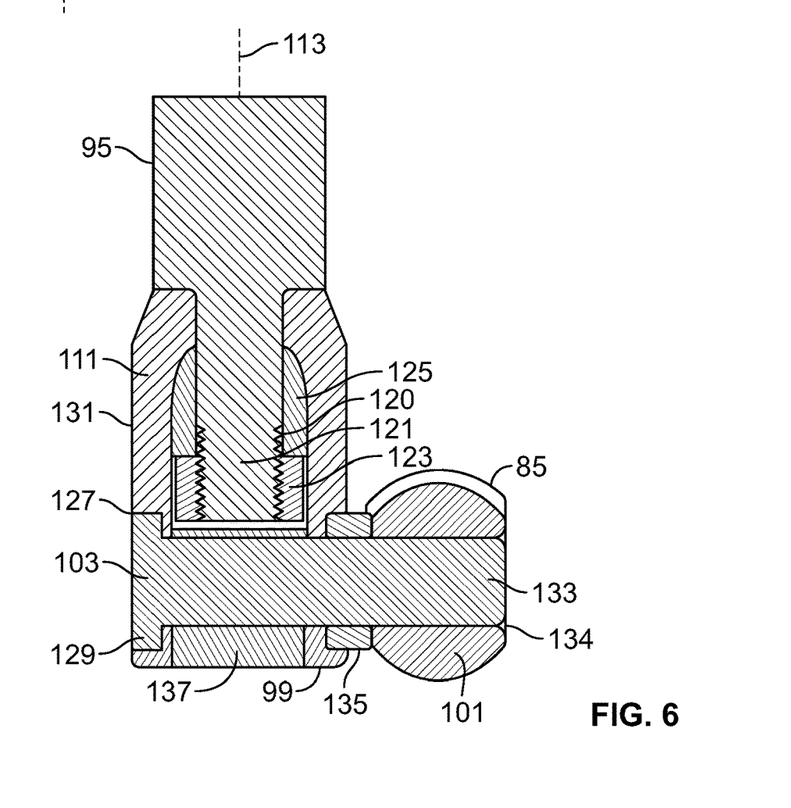
FIG. 6 is a cross sectional view of the arm connection area of FIG. 5, taken along A-A of FIG. 8.
Figure 6A:
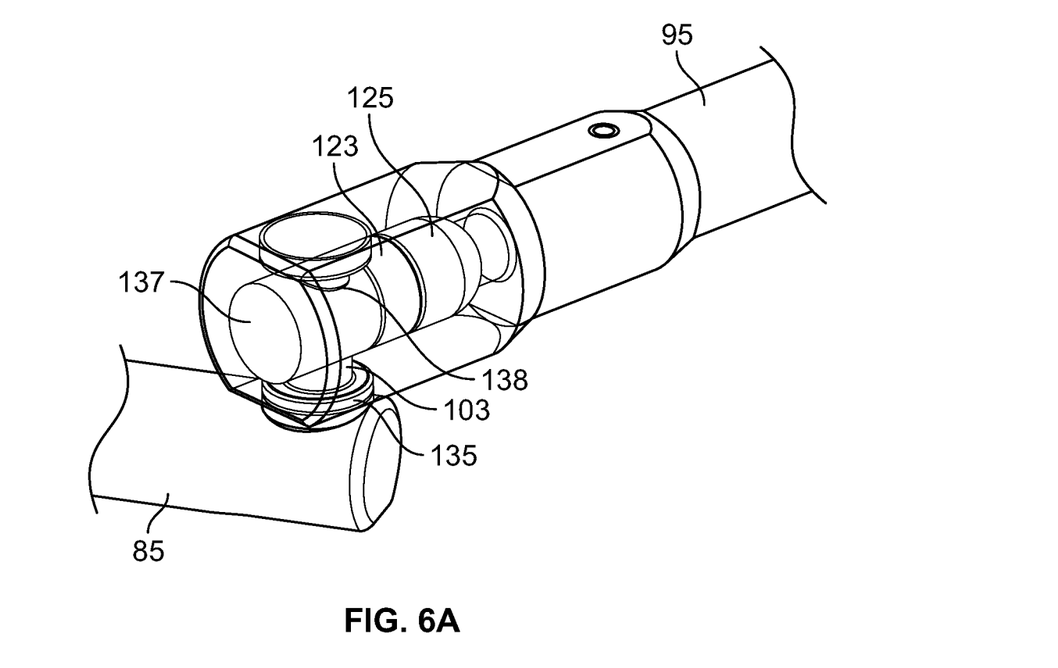
FIG. 6A is a transparency view of the arm connection area of FIGS. 5 and 6.
Figure 7:
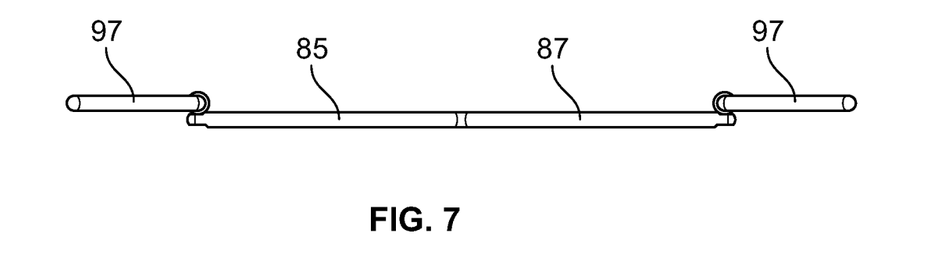
FIG. 7 is an end view of the one-piece frame of FIG. 3, and as shown in FIG. 8.
Figure 8:
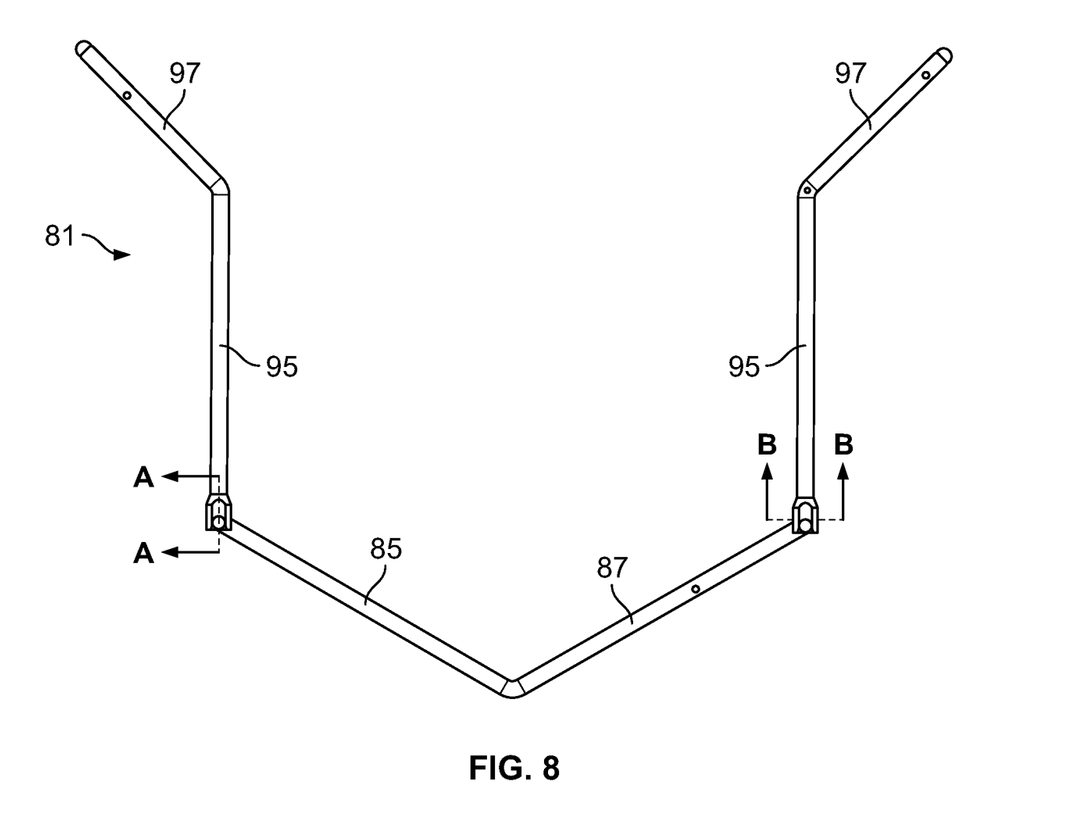
FIG. 8 is a top view of the one-piece frame of FIG. 3.
Figure 9:
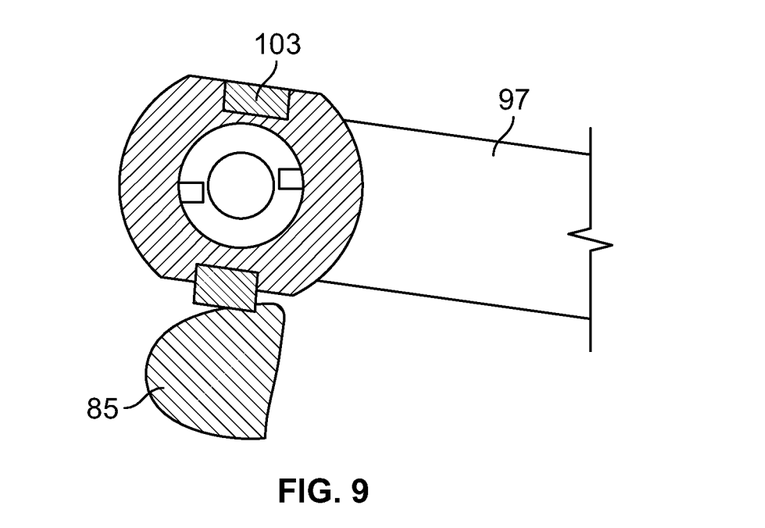
FIG. 9 is a cross sectional view of the arm connection area of FIG. 5, taken along B-B of FIG. 8.
Figure 10:
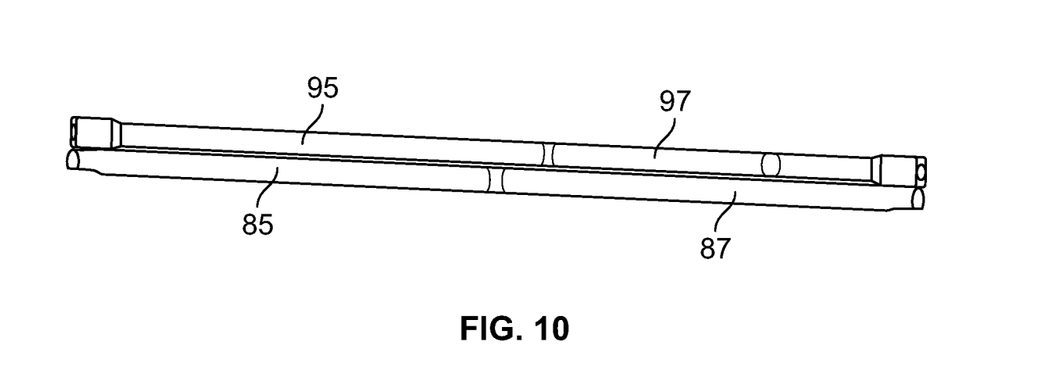
FIG. 10 is a side view of the one-piece frame of FIG. 8 in a folded configuration.
Figure 11:
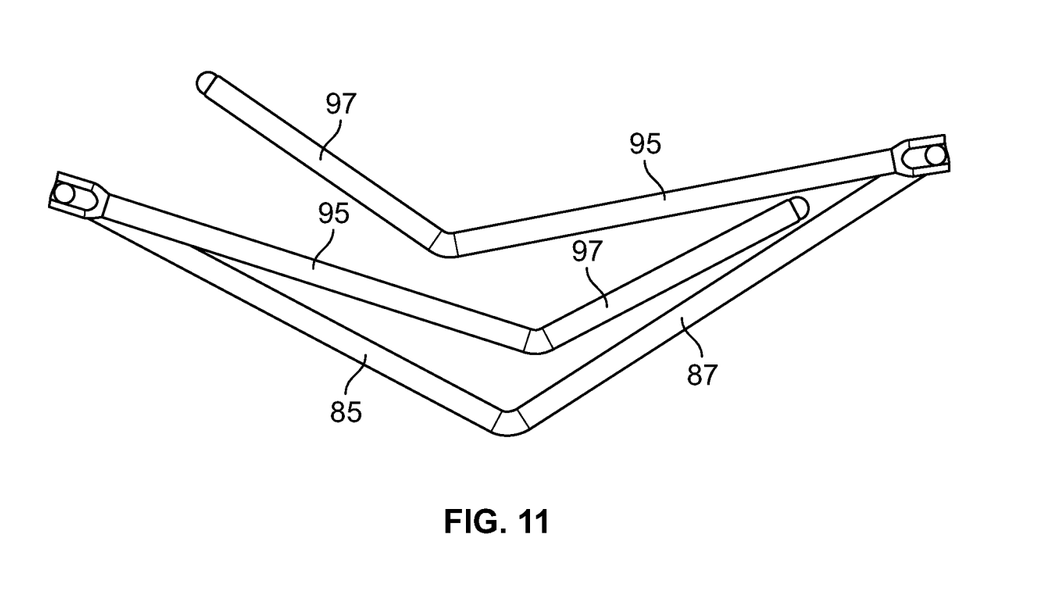
FIG. 11 is a top view of the one-piece frame of FIG. 8 in a folded configuration.

Referring now to FIG. 6, end portion 99 of arm portion 95 includes a threaded cylindrical end 121 having threads 120 which receive a tightening screw-on nut 123. Middle section 111 is placed over threaded end 121 allowing the threaded end 121 to freely rotate relative to middle section 111. Nut 123 is then tightened onto threaded end 121 to retain middle section 111 into position as shown in FIG. 6, and to allow rotation of middle section 111 about axis 113. A bushing 125 is positioned within middle section 111 and engages the end 121. Bushing 125 engages the front end of nut 123 as middle section 111 rotates relative to arm portion 95.

Middle section 111 extends outwardly from threaded end 121 and provides an aperture 127 for receiving pin 103. Pin 103 freely rotates within aperture 127.

As shown in FIG. 6, pin 103 includes an expanded end 129 which is shaped so as to control the depth of pin 103 within aperture 127. The expanded end 129 of pin 103 is maintained flush with the outer surface 131 of middle section 111.

The opposite end 133 of pin 103 is secured to end 101 of extension arm 85 by, for example, a welding securement 134. Between end 101 and end 99, a shim 135 may be positioned in order to set the amount of clearance between extension arm 85 and end portion 99. In addition, a screw-on plug 137 may be placed at the end portion 99 and serves as a bushing for pin 103.

Screw-on plug 137 includes a cylindrical opening 138 to receive the pin 103. That is, the nut 123 is tightened first in order to hold the middle section 111 onto the arm portion 95; then the plug 137 is pressed up into the middle section; and then the pin 103 is pushed into the middle section 111 from left to right passing through the plug 137 and on into the end 101 of arm 85 for secure welding at 134 to the end 101. The plug 137 provides a bushing surface for the pin 103.

The articulated frame 81 may be folded or collapsed as shown in FIGS. 7-11. In particular, arm portions 95 may fold inwardly toward respective extension arms 85, 87 by rotating about its respective axis 105. Such folding may result in arm portions 95 aligning align with or coming in close proximity to respective extension arm 85, 87 to achieve the folded or collapsed arrangement shown in FIG. 11.

Various embodiments have been described herein by way of example and not by way of limitation in the accompanying figures. For clarity of illustration, exemplary elements illustrated in the figures may not necessarily be drawn to scale. In this regard, for example, the dimensions of some of the elements may be exaggerated relative to other elements to provide clarity. Furthermore, where considered appropriate, reference labels have been repeated among the figures to indicate corresponding or analogous elements.

While the present disclosure has described certain embodiments, those skilled in the art understand that various changes may be made and equivalents may be substituted without departing from the intended scope of protection. In addition, many modifications may be made to adapt a particular situation or material to the teachings of the present disclosure without departing from its scope. Therefore, it is intended that the present disclosure not be limited to the particular embodiment or embodiments disclosed, but encompass all embodiments falling within the scope of the appended claims.

What is claimed is:

1. A surgical retractor system for a surgical site, the surgical retractor system comprising:
    a retractor frame assembly configured to be secured to an operating table; and
    a one-piece frame attached to the retractor frame assembly to from an enclosed frame that encloses the surgical site, said one-piece frame including:
        an extension arm frame comprised of a pair of extension arms each having a first end and a second end, said first end of each extension arm being secured to the first end of the other extension arm at a bend; and
        a pair of lateral arms, each lateral arm having a proximal end attached to the retractor frame assembly and a distal end rotatably coupled to a respective second end of said pair of extension arms to provide rotation of each lateral arm relative to the extension arm frame.

2. The surgical retractor system of claim 1, wherein each lateral arm comprises two arm sections, each arm section being substantially straight and connected to the other arm section at an angle.

3. The surgical retractor system of claim 1, wherein each lateral arm is pivotably coupled to its respective extension arm via a pin that permits 360 degree rotation.

4. The surgical retractor system of claim 1, wherein each lateral arm has a longitudinal axis and is rotatably mounted relative to its respective extension arm for rotation about said longitudinal axis.

5. The surgical retractor system of claim 1, further comprising a retractor blade connected to the retractor assembly.

6. The surgical retractor system of claim 1, wherein said extension arms are substantially straight along their longitudinal axis.

7. The surgical retractor system of claim 1, wherein said first end of each extension arm is secured to the first end of the other extension arm to form a V-shaped configuration.

8. The surgical retractor system of claim 1, wherein the retractor frame assembly comprises a vertical post secured to an operating table.

9. The surgical retractor system of claim 8, wherein:
    the retractor frame assembly further comprises a cross bar secured to the operating table via the vertical post; and
    the one-piece frame is attached to the retractor frame assembly via the cross bar.

10. An articulated frame for use with a surgical retractor system comprising a retractor frame assembly and a plurality of retractor blades, the articulated frame comprising:
    a first lateral arm having a proximal end to be coupled to the retractor frame assembly of the surgical retractor system;
    a second lateral arm having a proximal end to be coupled to the retractor frame assembly of the surgical retractor system; and
    an extension arm frame comprising a first end and a second end, wherein the first end of the extension arm frame is pivotably coupled to a distal end of the first lateral arm to provide rotation of the first lateral arm relative to the extension arm frame, and wherein the second end of the extension arm frame is pivotably coupled to a distal end of the second lateral arm to provide rotation of second lateral arm relative to the extension arm frame.

11. The articulated frame of claim 10, wherein the extension arm frame comprises a bend between the first end and the second end of the extension arm frame.

12. The articulated frame of claim 10, wherein:
    the extension arm frame comprises a first extension arm and a second extension arm; and
    the first extension arm is coupled to the second extension arm at a bend of the extension arm frame.

13. The articulated frame of claim 12, wherein:
    the first extension arm is substantially straight along its longitudinal axis; and
    the second extension arm is substantially straight along its longitudinal axis.

14. The articulated frame of claim 10, wherein:
    the first lateral arm comprises a first arm section and a second arm section; and
    the first arm section is connected to the second arm section at a bend of the first lateral arm.

15. The articulated frame of claim 14, wherein:
    the first arm section of the first lateral arm is substantially straight; and
    the second arm section of the first lateral arm is substantially straight.

16. The articulated frame of claim 14, wherein:
    the second lateral arm comprises a first arm section and a second arm section;

the first arm section of the second lateral arm is connected to the second arm section of the second lateral arm at a bend of the second lateral arm;

the first arm section of the second lateral arm is substantially straight; and the second arm section of the second lateral arm is substantially straight.

17. The articulated frame of claim 10, wherein the first lateral arm is pivotably coupled to the extension arm frame via a pin that permits 360 degree rotation of the first lateral arm about a longitudinal axis of the pin.

18. The articulated frame of claim 10, wherein the first lateral arm has a longitudinal axis and is rotatably mounted relative to the extension arm frame for rotation about said longitudinal axis.

* * * * *